(12) United States Patent
Honkanen

(10) Patent No.: US 7,332,335 B2
(45) Date of Patent: Feb. 19, 2008

(54) DECREASING CELL PROLIFERATION BY DECREASING LEVELS OF PP5

(75) Inventor: Richard E. Honkanen, Mobile, AL (US)

(73) Assignee: South Alabama Medical Science Foundation, Mobile, AL (US)

( * ) Notice: Subject to any disclaimer, the term of this patent is extended or adjusted under 35 U.S.C. 154(b) by 552 days.

(21) Appl. No.: 10/358,851

(22) Filed: Feb. 5, 2003

(65) Prior Publication Data

US 2003/0220279 A1    Nov. 27, 2003

(51) Int. Cl.
  *C12N 5/00*   (2006.01)
  *C12Q 1/68*   (2006.01)
  *C12P 19/34*   (2006.01)
  *C07H 21/02*   (2006.01)
  *C07H 21/04*   (2006.01)

(52) U.S. Cl. ................ 435/375; 435/6; 435/91.1; 435/91.31; 536/23.1; 536/24.5

(58) Field of Classification Search .............. 435/6, 435/91.1, 91.31, 455, 458, 375; 536/23.1, 536/24.5; 514/1, 2, 44
See application file for complete search history.

(56) References Cited

U.S. PATENT DOCUMENTS 5,225,326 A    7/1993 Bresser

OTHER PUBLICATIONS

Branch, A., Trends in Biochem. Sci., vol. 23, pp. 45-50 (1998).*
Crooke, S., Antisense Res. and Application,Chapter 1, pp. 1-50, Publ. by Springer-Verlag, Ed. by S. Crooke (1989).*
Peracchi, A., Rev. Med. Virol., vol. 14, pp. 47-64 (2004).*
Chirila, T. et al., Biomaterials, vol. 23, pp. 321-342 (2002).*
Agrawal, S. et al., Molecular Med. Today, vol. 6, pp. 72-81 (2000).*
Honkanen, R., FEBS, vol. 330, No. 3, pp. 283-286 (1993).*
Ruiting et al., Chinese Med. J., vol. 93, No. 3, pp. 183-187 (1980).*
de Jong, R.S. et al., British J. Cancer, vol. 79, No. 5/6, pp. 882-887 (1999).*
Agarwal, M.L., et al., Proc Natl Acad Sci USA 92:8493 (1995).
Ammala, C., et al., Proc Natl Acad Sci USA 91:4343-4347 (1994).
Bastians, H., et al., J Cell Sci 109:2865 (1996).
Bialojan, A., et al., Biochem J 256:283 (1988).
Brewis, N.D., et al., EMBO J 12:987 (1993).
Cairns, J., et al., J of Bio Chem 269(12):9176-9183 (1994).
Chen, M.X., et al., EMBO J 13(18):4278-4290 (1994).
Chernova, O. B., et al., Trends Bio Sci 20:431 (1995).
Cohen, P., Annu Rev Biochem 58:453 (1989).
Cohen, P., et al., FEBS Lett 268:355 (1990).
Cohen, P., et al., Trends Bio Sci 15:98 (1990).
Cohen, P., TIBS 22 : 245-251 (1997).
Duttaroy, A., et al., J Cell Biochem 64:434 (1997).
Dynlacht, B.D., Nature 389:149 (1997).
Egloff, M.P., et al., J Mol Biol 254:942 (1995).
Elledge, S.J., et al., Curr Opin Cell Biol 6:847 (1994).
Gomyo, Y., et al., Cancer 79:2067 (1997).
Gottlieb, T.M., et al., Biochem Biophys Acta 1287:77 (1996).
Gu., Y., et al., Nature 366:707 (1993).
Harper, J.W., et al., Mol Biol Cell 6:387 (1995).
Honkanen, R.E., et al., J Biol Chem 265:19401 (1990).
Honkanen, R.E., et al., Toxicon 32:339 (1994).
Hsiao, M., et al., Biochem Biophys Res Commun 233:329 (1997).
Hunter, T., et al., Cell 79:573 (1994).
Lamb, J.R., et al., Trends in Bio Sci 20:257 (1995).
Macleod, K.F., et al., Genes Dev 9:935 (1995).
Peter, M., et al., Cell 79:181 (1994).
Scully, R., et al., Cell 90:425 (1997).
Sherr, C.J., Cell 79:551 (1994).
Sogawa, K., et al., Cancer Letters 89:1-6 (1995).
Sogawa, K., et al., Res Commun Mole Path Pharm 86(3):375-378 (1994).
Somasundaram, K., et al., Nature 389:187 (1997).
Wera, S., et al., Biochem J 311:17-29 (1995).
Xiong, Y., et al., Nature 366:701 (1993).
Yamada, T., et al., Res Comm Mole Path Pharm 86(1):125-128 (1994).
Yin, Y., et al., Cell 70:937 (1992).
Zeng, Y.X., et al., Oncogene 12:1557 (1996).
El-Deiry, W.S., et al., Cell 75:817-825 (1993).
Harper, J.W., et al., Cell 75:805-816 (1993).
Becker, W., et al., J Bio Chem 269(36):22586-22592 (1994).
Chinkers, M., Proc Natl Acad Sci USA 91:11075-11079 (1994).
Skinner, J., et al., J Biol Chem 272(36):22464-22471 (1997).
Branch, TIBS 23:45-50 (1998).
Gerwitz et al., PNAS 93:3161-3163 (1996).
Rojanasakul, Advanced Drug Delivery Reviews 18:115-131 (1996).
Milligan et al., J Medicinal Chem 36:1923-1937 (1993).

* cited by examiner

*Primary Examiner*—Jane Zara
(74) *Attorney, Agent, or Firm*—Peter Rogalskyj; Karla M. Weyand

(57) ABSTRACT

The invention provides a method of increasing expression of $p21^{WAF1/Cip1}$ in cells to decrease proliferation of the cells, the method comprising decreasing levels of PP5 protein in the cells. The invention further provides a method of treating or preventing an abnormal condition resulting from a defect in a tumor suppressor gene in a subject that results in decreased induction of $p21^{WAF1/Cip1}$ in the cells of the subject, the method comprising administering to the subject an amount of a compound effective to decrease levels of PP5 protein in the cells of the subject.

5 Claims, 5 Drawing Sheets

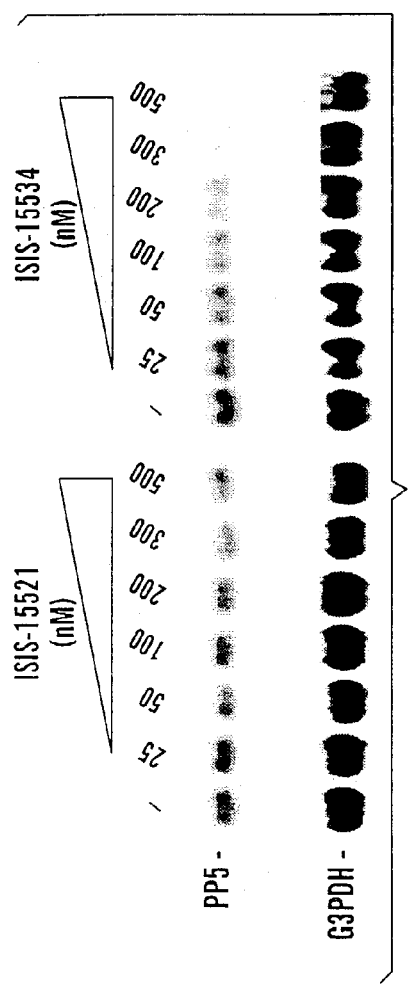
FIG. 4
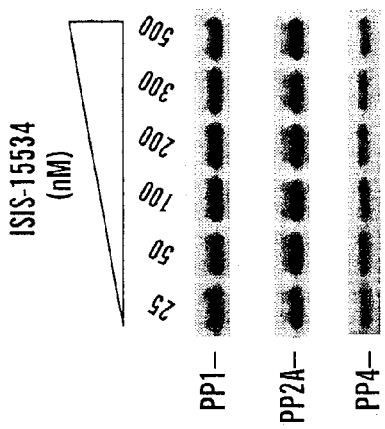
FIG. 6
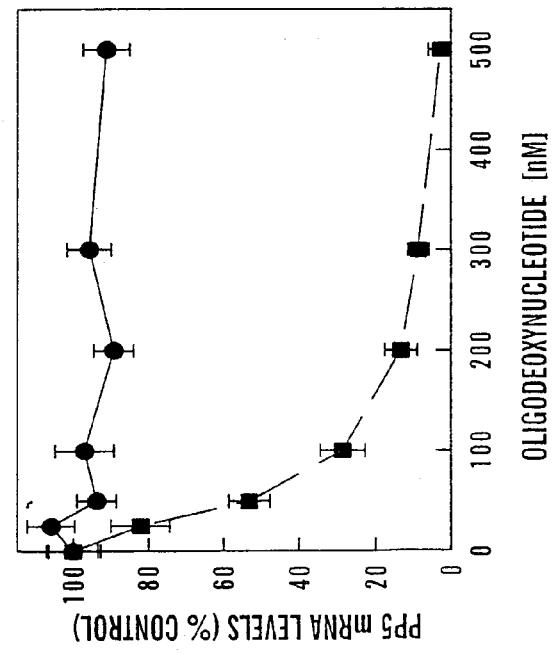
FIG. 7
FIG. 5

FIG. 11
FIG. 10
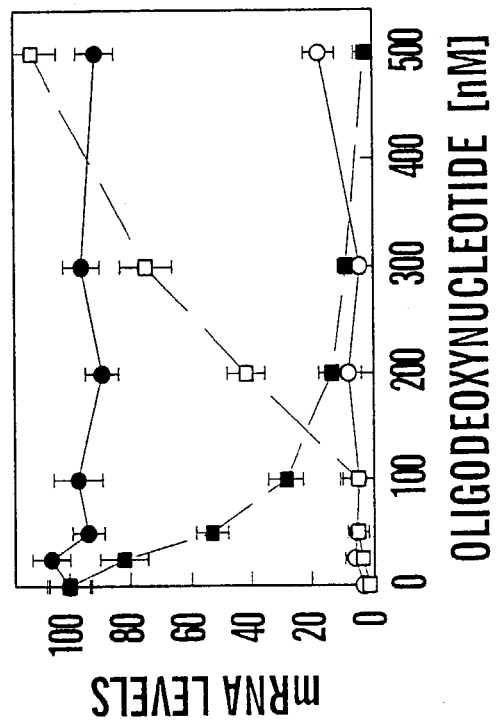
FIG. 12

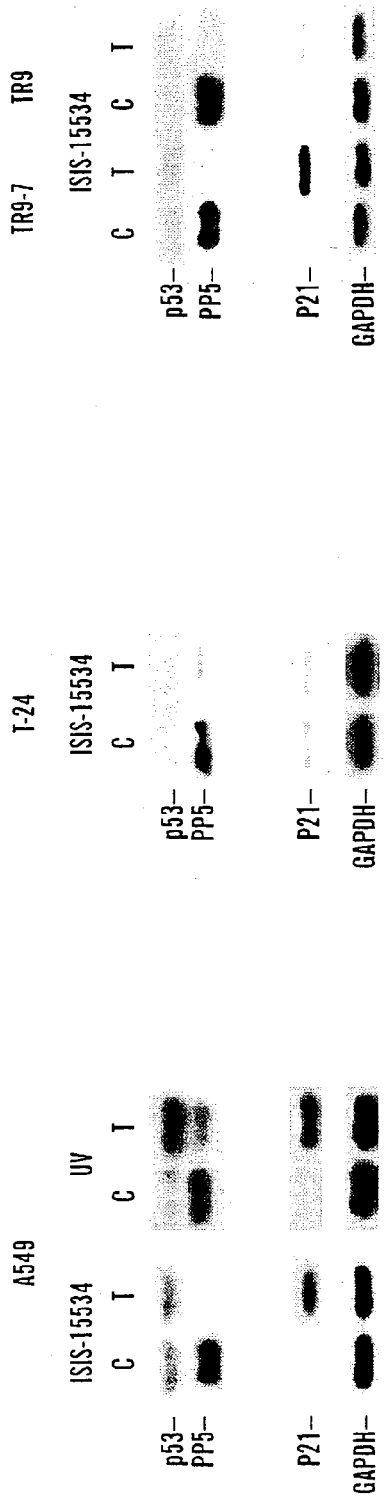
FIG. 13
FIG. 14
FIG. 15
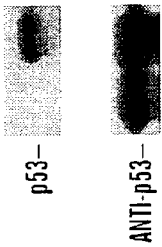
FIG. 17
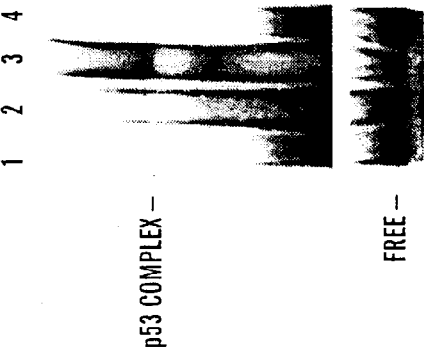
FIG. 16

DECREASING CELL PROLIFERATION BY DECREASING LEVELS OF PP5

This invention was made with support under National Institutes of Health Grant No. CA60750.

FIELD OF THE INVENTION

The subject invention is directed generally to a method for decreasing cell proliferation, and more particularly to decreasing cell proliferation by inhibition of PP5 gene expression.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

Passage from G1-into S-phase of the eukaryotic cell cycle is dependent on the successive activation and inactivation of several G1-cyclin-dependent protein kinases (G1-Cdks). These G1-Cdks function to coordinate transcription control with the activity of numerous cell cycle regulatory proteins and genes, whose products mediate DNA synthesis and other mechanical aspects of the cell cycle (Dynlacht 1997). During normal cell cycle progression, the temporal activation of individual G1-Cdks is dictated primarily by the expression of cognate cyclins together with both activating and inactivating phosphorylation. In addition G1-Cdk activity is also affected by the interaction with regulatory proteins, such as $p21^{WAF1/Cip\ 1}$, which inhibit Cdks as part of a complex cellular response to genotoxic stress. This additional layer of regulation affords cells with damaged DNA the ability to interrupt or delay cell cycle progression at "G1- and G2-cell cycle checkpoints" (Peter and Herskowitz 1994; Elledge and Harper 1994; Hunter and Pines 1994).

The $p21^{WAF1/Cip\ 1}$ gene, also known as pic1, Sdil or 20CAP (Duttaroy et al. 1997; Gu et al. 1993), encodes an inhibitor of most cyclin-dependent kinases (Xiong et al. 1993; Harper et al. 1995) and has been implicated as a growth arrest mediator in p53-tumor suppression. In response to DNA damage (Macleod et al. 1995; Gottlieb and Oren 1996) or alterations in cellular homeostasis (Chernova et al. 1995), normal cells can respond by increasing the induction of p53. Although the mechanism(s) leading to the induction of p53 are unclear, p53 acts as a transcription factor, and increased expression of wild-type p53 stimulates the synthesis of $p21^{WAF1/Cip\ 1}$. In turn, $p21^{WAF1/Cip\ 1}$ inhibits the activity of cyclin D/Cdk4,6 and/or cyclinE/Cdk2, preventing the phosphorylation of the retinoblastoma protein (Rb) and inducing cell growth arrest late in the G1 stage of the cell cycle (Chernova et al. 1995). Studies in p53 deficient cells (Agarwal et al. 1995; Yin et al. 1992) indicate that the increased expression of p53 alone (i.e. in the absence of DNA damage) stimulates the synthesis of $p21^{WAF1/Cip\ 1}$ and growth arrest in the G1 phase of the cell cycle. Nonetheless, recent studies indicate that $p21^{WAF1/Cip\ 1}$ is also required for arrest of the cell cycle by the tumor-suppressor protein BRCA1, which is associated with hereditary breast and ovarian cancer (Somasundaram et al. 1997; Scully et al. 1997), and $p21^{WAF1/Cip\ 1}$ induction has been implicated in other physiological processes, such as cell differentiation and senescence, via p53 independent mechanisms (Zeng and el-Deiry 1996).

In vivo, the reversible phosphorylation of serine residues is believed to influence the biological activity of p53, and p53 is phosphorylated at multiple sites (Takenaka et al. 1995; Hecker et al. 1996; Mayr et al. 1995). Increased phosphorylation of ser 309 and 370 enhances the DNA binding activity of p53, and phosphorylation of serines 6, 17 and 34 is important for transcriptional activity (Takenaka et al. 1995; Hecker et al. 1996; Mayr et al. 1995).

Since virtually all known examples of transcriptional control during the cell cycle involve phosphorylation and the G1-Cdks are serine/threonine (ser/thr) protein kinases, specific ser/thr protein phosphatases (PPases) may also participate in the regulation of cell cycle progression. In mammals, at least thirteen closely related enzymes, including four highly homologous isoforms of PP1 (PP1α, β, $γ_1$, $γ_2$), two isoforms of PP2A (PP2α,β), three isoforms of PP2B (α,β,γ), PP4, PP5, PP6 and PP7 have been identified, and any, or all, of these PPases may contribute to cell cycle regulation (Cohen 1997; Egloff et al. 1995; Brewis et al. 1993; Chen et al. 1994; Bastians and Ponstingl 1996). Of the known PPases, PP1, PP2A, PP4 and PP5 are sensitive to several natural toxins, such as okadaic acid (Bialojan and Takai 1988; Honkanen et al. 1994; Cohen et al. 1990b) and microcystin (Honkanen et al. 1990), and reports indicating that okadaic acid has tumor promoting activity have led to speculation that the toxin-sensitive PPases may regulate cell growth. In addition, preliminary studies indicate that tumor cells in log phase growth express higher levels of PP5 mRNA, and the presence of multiple tetratrico peptide repeat (TPR) sequences in PP5 suggest that PP5 may interact with other TPR containing proteins, many of which are involved in the regulation of cell cycle progression (Lamb et al. 1995).

Determining specific roles for any of the thirteen structurally related mammalian PPases has proven difficult due to: 1) the lack of substrate sensitivity demonstrated by most of these PPases in vitro; 2) the lack of truly specific inhibitors for individual PPases; and 3) complications in assessing the functions of numerous loosely associated ancillary proteins that regulate the activity of, impart substrate specificity to, and influence the cellular localization of individual PPases, in vivo (Walter and Mumby 1993; Shenolikar and Nairn 1991; Cohen 1989; Cohen et al. 1990a).

Since a predisposition to many forms of cancer has been attributed to defects in tumor suppressor genes that regulate the expression of the cyclin-dependent kinase inhibitor, $p21^{WAF1/Cip\ 1}$, any methods that can circumvent these defects could potentially be useful in treating and/or preventing cancer.

SUMMARY OF THE INVENTION

The subject invention provides such a method which involves the PP5 gene. More particularly, the invention provides a method of increasing expression of $p21^{WAF1/Cip\ 1}$ in cells to decrease proliferation of the cells, the method comprising decreasing levels of PP5 protein in the cells. The invention further provides a method of treating or preventing an abnormal condition resulting from a defect in a tumor suppressor gene in a subject that results in decreased induction of $p21^{WAF1/Cip\ 1}$ in the cells of the subject, the method comprising administering to the subject an amount of a compound effective to decrease levels of PP5 protein in the cells of the subject.

BRIEF DESCRIPTION OF THE DRAWINGS

These and other features and advantages of this invention will be evident from the following detailed description of preferred embodiments when read in conjunction with the accompanying drawings in which:

FIG. 4 shows,the inhibition of PP5 mRNA levels by increasing concentrations of ISIS 15534 and the mismatched control ODN, ISIS 15521;

FIG. 5 shows the quantification of PP5 mRNA levels after normalization to G3PDH following treatments with increasing concentrations of ISIS 15534 and the mismatched control ODN, ISIS 15521;

FIG. 6 shows the Western blot analysis of PP5 protein levels in A549 cells following treatment with ISIS 15534 and the mismatched control ODN, ISIS 15521;

FIG. 7 shows the target-specific inhibition of PP5 mRNA by ISIS 15534;

FIGS. 10 and 11 illustrate the inhibition of PP5 expression in relation to $p21^{WAF1/Cip\,1}$ expression after treatment with the mismatch control ODN ISIS 15521 (FIG. 10) and ISIS 15534 (FIG. 11);

FIG. 12 shows the quantification of PP5 mRNA and $p21^{WAF1/Cip\,1}$ mRNA levels after normalization to G3PDH mRNA levels following treatment with increasing concentrations of ISIS 15534 and the mismatched control ODN, ISIS 15521;

FIG. 13 shows the effect of UV-radiation treatment or treatment with ISIS 15534 on the expression of p53, PP5, and $p21^{WAF1/Cip\,1}$ in p53 competent human lung carcinoma cells (A549 cells);

FIG. 14 shows the effect of ISIS 15534 on the expression of p53, PP5, and $p21^{WAF1/Cip\,1}$ in p53 deficient bladder carcinoma cells (T-24 cells);

FIG. 15 shows the effect of ISIS 15534 on the expression of p53, PP5, and $p21^{WAF1/Cip\,1}$ in p53 null-human fibroblasts (TR9 cells) and TR9 cells containing tetracycline-regulated transactivator and operator plasmids to control the expression of wild-type p53 (TR9-7 cells);

FIG. 16 shows that the inhibition of PP5 expression enhances p53 binding to DNA; and FIG. 17 shows the increased phosphorylation of p53 following treatment with ISIS 15534.

DETAILED DESCRIPTION OF THE INVENTION

Figure 1:
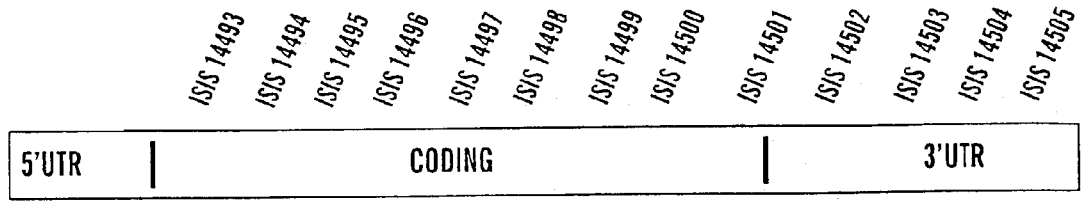
FIG. 1 shows the relative positioning of the predicted hybridization sites within the human PP5 mRNA of 13 antisense ODNs.

The subject invention is based on the discovery that decreasing levels of PP5 protein in a cell (such as by decreasing PP5 gene expression) can induce expression of $p21_{WAF1/Cip\,1}$, a known inhibitor of most cyclin-dependent kinases. The induced expression of $p21^{WAF1/Cip\,1}$ leads to growth arrest and, therefore, decreasing levels of PP5 protein in a cell can be used to decrease cell proliferation. This is especially advantageous in cancer cells and other hyperproliferative cell disorders.

The invention thus provides a method of increasing expression of $p21^{WAF1/Cip\,1}$ in cells to decrease proliferation of the cells, the method comprising decreasing levels of PP5 protein in the cells.

Levels of PP5 protein in the cells can be decreased by various methods, at the gene and protein levels. In one embodiment, the levels are decreased by decreasing PP5 gene expression of the PP5 protein in the cells. This can be accomplished by exposing the cells to a compound which decreases PP5 gene expression of the PP5 protein. The compound could be, for example, an antisense oligonucleotide targeted to the PP5 gene. This aspect of the subject invention is discussed in further detail below, where particular antisense oligonucleotides targeted to the PP5 gene include the antisense oligonucleotides having a nucleotide sequence selected from the group consisting of: SEQ ID NO: 1, SEQ ID NO: 3, SEQ ID NO: 4, SEQ ID NO: 5, SEQ ID NO: 6, SEQ ID NO: 8, and SEQ ID NO: 9.

In a similar embodiment, the compound which decreases PP5 gene expression of the PP5 protein could be a ribozyme, which is a special category of antisense RNA molecule having a recognition sequence complementary to the mRNA encoding the PP5. A ribozyme not only complexes with a target sequence via complementary antisense sequences, but also catalyzes the hydrolysis, or cleavage, of the template mRNA molecule. The expression of the PP5 protein is therefore prevented.

Other methods for decreasing PP5 gene expression could also involve site-directed mutagenesis of the PP5 gene to prevent expression of the PP5 protein, or various gene therapy techniques.

Levels of PP5 protein in the cell can also be decreased by exposing the cells to an inhibitor of the PP5 protein. Currently known inhibitors of PP5 include, for example, okadaic acid and microcystin. Other inhibitors of the PP5 protein could also readily be identified by various screening methods used in the art. In addition to chemical inhibitors, peptide inhibitors could also be identified with currently known screening methods (for example, using phage display libraries and other peptide screening methods).

Since the method of the subject invention is a method of increasing expression of $p21^{WAF1/Cip\,1}$ in cells to decrease proliferation of the cells, the cells of interest are hyperproliferative cells. Such cells include, for example, cancer cells. In 50% of human cancers, the cancer cells harbor a defect in a tumor suppressor gene that results in decreased induction of $p21^{WAF1/Cip\,1}$. The tumor suppressor gene may be, for example, the p53 gene or the BRCA1 gene. Defects in each of these genes result in decreased induction of $p21^{WAF1/Cip\,1}$, which is associated with aberrant growth arrest and hyperproliferation of the cells. Therefore, decreasing levels of PP5 protein in these cells can be used to decrease cell proliferation.

The invention further provides a method of treating or preventing an abnormal condition resulting from a defect in a tumor suppressor gene in a subject that results in decreased induction of $p21^{WAF1/Cip\,1}$ in the cells of the subject, the method comprising administering to the subject an amount of a compound effective to decrease levels of PP5 protein in the cells of the subject. As above, the compound may decrease levels of PP5 protein by decreasing PP5 gene expression of the PP5 protein, or by inhibiting the PP5 protein.

The method is useful where the abnormal condition is a hyperproliferative disorder. Examples of abnormal proliferative conditions are hyperproliferative disorders such as cancers, tumors and hyperplasias, including smooth muscle cell proliferation in the blood vessels, such as stenosis or restenosis following angioplasty.

In a presently preferred embodiment, the invention employs oligonucleotides targeted to nucleic acids encoding protein phosphatase 5 (PP5). The relationship between an oligonucleotide and its complementary nucleic acid target to which it hybridizes is commonly referred to as "antisense". "Targeting" an oligonucleotide to a chosen nucleic acid target, in the context of this invention, is a multistep process. The process usually begins with identifying a nucleic acid sequence whose function is to be modulated. In the subject invention, this may be, for example, the cellular gene (or mRNA made from the gene) for PP5; i.e., the target is a nucleic acid encoding protein phosphatase 5, the PP5 gene, or mRNA expressed from the protein phosphatase 5 gene. The targeting process also includes determination of a site or sites within the nucleic acid sequence for the oligonucleotide interaction to occur such that the desired effect, modulation of gene expression, will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of protein phosphatase gene expression is presently the preferred form of modulation. This modulation can be measured in ways which are routine in the art, for example by Northern blot assay of mRNA expression or Western blot assay of protein expression as taught in the examples of the instant application. Effects on cell proliferation can also be measured, as taught in the examples of the instant application. "Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In preferred embodiments of this invention, oligonucleotides are provided which are targeted to mRNA encoding protein phosphatase 5 (PP5). In accordance with this invention, persons of ordinary skill in the art will understand that mRNA includes not only the coding region which carries the information to encode a protein using the three letter genetic code, including the translation start and stop codons, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated in accordance with this invention which are targeted wholly or in part to these associated ribonucleotides as well as to the coding ribonucleotides. In preferred embodiments, the oligonucleotide is targeted to a translation initiation site (AUG codon) or sequences in the coding region, 5' untranslated region or 3'-untranslated region of mRNA encoding human PP5. The functions of mRNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with PP5 expression.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

Certain preferred oligonucleotides of this invention are chimeric oligonucleotides. "Chimeric oligonucleotides" or "chimeras", in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Consequently, comparable results can often be obtained with shorter oligonucleotides when chimeric oligos are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one preferred embodiment, a chimeric oligonucleotide comprises at least one region modified to increase target binding affinity and, usually, a region that acts as a substrate for RNAse H. Affinity of an oligonucleotide for its target (in this case a nucleic acid encoding protein phosphatase 5) is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In a more preferred embodiment, the region of the oligonucleotide which is modified to increase PP5 mRNA binding affinity comprises at least one nucleotide modified at the 2' position of the sugar, most preferably a 2'-O-alkyl, 2'-O-alkyl-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance antisense oligonucleotide inhibition of PP5 gene expression. RNAse H is a cellular endonuclease that cleaves the RNA strand of RNA: DNA duplexes; activation of this enzyme therefore results in cleavage of the RNA target, and thus can greatly enhance the efficiency of antisense inhibition. Cleavage of the RNA target can be routinely demonstrated by gel electrophoresis.

In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance, is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. A discussion of antisense oligonucleotides and some desirable modifications can be found in De Mesmaeker et al. 1995.

Specific examples of some preferred oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—$NH$—$O$—$CH_2$, $CH_2$—$N(CH_3)$—$O$—$CH_2$ [known as a methylene(methylimino) or MMI backbone], $CH_2$—$O$—$N(CH_3)$—$CH_2$, $CH_2$—$N(CH_3)$—$N(CH_3)$—$CH_2$ and $O$—$N(CH_3)$—$CH_2$—$CH_2$ backbones, wherein the native phosphodiester backbone is represented as $O$—$P$—$O$—$CH_2$). The amide backbones disclosed by De Mesmaeker et al. 1995 are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al. 1991). Oligonucleotides may also contain one or more substituted sugar moieties. Preferred oligonucleotides comprise one of the following at the 2' position: OH, SH, $SCH_3$, F, OCN, $OCH_3OCH_3$, $OCH_3O$ $(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy (also known in the art as O-alkyl-O-alkyl), substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—$CH_2CH_2OCH_3$, also known as 2'-O—(2-methoxyethyl) or 2'-MOE] (Martin et al. 1995). Other preferred modifications include 2'-methoxy (2'-O—$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-me pyrimidines, particularly 5-methylcytosine (also referred to as 5-methyl-2'deoxycytosine and often referred to in the art as 5-me-C), 5-hydroxymethylcytosine (HMC), glycosyl HMC and gentobiosyl HMC, as well as synthetic nucleobases, e.g., 2-aminoadenine, 2-thiouracil, 2-thiothymine, 5-bromouracil, 5-hydroxymethyluracil, 8-azaguanine, 7-deazaguanine, $N^6$(6-aminohexyl)adenine and 2,6-diaminopurine (Kornberg 1980; Gebeyehu et al. 1987). A "universal" base known in the art, e.g., inosine, may be included. 5-me-C substitutions have been shown to increase nucleic acid duplex stability by 0.6-1.2° C. (Sanghvi 1993b) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al. 1989), cholic acid (Manoharan et al. 1994), a thioether, e.g., hexyl-S-tritylthiol (Manoharan et al. 1992; Manoharan et al. 1993), a thiocholesterol (Oberhauser et al. 1992), an aliphatic chain, e.g., dodecandiol or undecyl residues (Saison-Behmoaras et al. 1991; Kabanov et al. 1990; Svinarchuk et al. 1993), a phospholipid, a polyamine or a polyethylene glycol chain (Manoharan et al. 1995a), or adamantane acetic acid (Manoharan et al. 1995b). Oligonucleotides comprising lipophilic moieties, and methods for preparing such oligonucleotides are known in the art; see, for example, U.S. Pat. No. 5,138,045, No. 5,218,105 and No. 5,459,255.

It is not necessary for all positions in a given oligonucleotide to be uniformly modified, and in fact more than one of the aforementioned modifications may be incorporated in a single oligonucleotide or even at a single nucleoside within an oligonucleotide.

The compounds and/or inhibitors used in the methods of the subject invention encompass any pharmaceutically acceptable salts, esters, or salts of such esters, or any other compound/inhibitor which, upon administration to an animal including a human, is capable of providing (directly or indirectly) the biologically active metabolite or residue thereof. Accordingly, for example, the disclosure is also drawn to prodrugs and pharmaceutically acceptable salts of the oligonucleotides used in the subject invention, pharmaceutically acceptable salts of such prodrugs, and other bioequivalents.

In regard to prodrugs, the oligonucleotides of the invention may additionally or alternatively be prepared to be delivered in a prodrug form. The term prodrug indicates a therapeutic agent that is prepared in an inactive form that is converted to an active form (i.e., drug) within the body,or cells thereof by the action of endogenous enzymes or other chemicals and/or conditions. In particular, prodrug versions of the oligonucleotides used in the subject invention are prepared as SATE [(S-acetyl-2-thioethyl) phosphate] derivatives according to the methods disclosed in WO 93/24510 to Gosselin et al., published Dec. 9, 1993.

In regard to pharmaceutically acceptable salts, the term pharmaceutically acceptable salts refers to physiologically and pharmaceutically acceptable salts of the oligonucleotides used in the subject invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al. 1977). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions used in the subject invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, the inorganic acids such as hydrochloric acid, hydrobromic acid, sulfuric acid or phosphoric acid, and the organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides used in the method of the subject invention preferably are from about 8 to about 50 nucleotides in length. In the context of this invention it is understood that this encompasses non-naturally occurring oligomers as hereinbefore described, preferably having 8 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the skill of the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In the context of this invention, to "expose" cells (including the cells of tissues) to an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

For therapeutics, methods of inhibiting hyperproliferation of cells and methods of preventing and treating abnormal proliferative conditions are provided. The formulation of therapeutic compositions and their subsequent administration is believed to be within the skill in the art. In general, for therapeutics, a patient suspected of needing such therapy is given an oligonucleotide in accordance with the invention, commonly in a pharmaceutically acceptable carrier, in amounts and for periods which will vary depending upon the nature of the particular disease, its severity and the patient's overall condition. The pharmaceutical compositions may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration. For oral administration, it has been found that oligonucleotides with at least one 2'-substituted ribonucleotide are particularly useful because of their absorption and distribution characteristics (see U.S. Pat. No. 5,591,721 of Agrawal et al.). Oligonucleotides with at least one 2'-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

In addition to such pharmaceutical carriers, cationic lipids may be included in the formulation to facilitate oligonucleotide uptake. One such composition shown to facilitate uptake is Lipofectin (BRL, Bethesda Md.).

Dosing is dependent on severity and responsiveness of the condition to be treated, with course of treatment lasting from several days to several months or until a cure is effected or a diminution of disease state is achieved. Optimal dosing' schedules can be calculated from measurements of drug accumulation in the body. Persons of ordinary skill can easily determine optimum dosages, dosing methodologies and repetition rates. Optimum dosages may vary depending on the relative potency of individual oligonucleotides, and can generally be calculated based on $IC_{50}$'s or $EC_{50}$'s in in vitro and in viva animal studies. For example, given the molecular weight of compound (derived from oligonucleotide sequence and chemical structure) and an effective dose such as an $IC_{50}$, for example (derived experimentally), a dose in mg/kg is routinely calculated.

Having explained the general concepts of the subject invention, a predisposition to many forms of cancer has been attributed to defects in tumor-suppressor genes, such as p53 and BRCA1, that regulate the expression of the cyclin-dependent kinase inhibitor, $p21^{WAF1/Cip\ 1}$ Employing antisense oligodeoxynucleotides capable of specifically inhibiting the expression of individual human serine/threonine protein phosphatases (PPases), the specific inhibition of PP5 gene expression is shown to have a marked antiproliferative effect on cells, characterized by induction of $p21^{WAF1/Cip\ 1}$ and the subsequent arrest of cell growth in the G1-phase of the cell cycle. Investigations into the mechanisms leading to growth arrest reveal that PP5 acts upstream of p53, influencing both the phosphorylation state and the ability of p53 to bind DNA, without an increase in p53 gene transcription. Together these studies indicate that PP5 plays an integral role in the regulation of p53 mediated induction of $p21^{WAF1/Cip\ 1}$ and provides the first direct evidence for the involvement of an individual mammalian PPase in G1-growth arrest. Furthermore, because the inhibition of PP5 gene expression induces the expression of $p21^{WAF1/Cip\ 1}$ and restores G1-checkpoint growth control, the studies show that inhibitors of PP5 may be useful as an alternate therapy for the treatment of human cancers harboring functional defects in pathways leading to the induction of $p21^{WAF1/Cip\ 1}$.

Materials and Methods

Gel Mobility Shift Assay: A549 cells cultured in 60 mm dishes were treated with mismatched control ODN ISIS 15521 or ISIS 15534 as described. Six hours after treatment, cells were collected and washed with ice-cold PBS, and incubated in buffer A (10 mM HEPES, pH 7.9, 10 mM KCl, 0.1 mM EDTA, 0.1 mM EGTA, 1 mM DTT, 0.5 mM PMSF) at 4° C. for 15 minutes. Cells were then lysed by adding 25 µl 10% NP-40 and vigorously vortexing for 10 seconds. Nuclei were precipitated by centrifuge and resuspended in ice-cold buffer B (20 mM HEPES, pH 7.9, 0.4 M NaCl, 1 mM EDTA, 1 mM EGTA, 1 mM DDT, 1 mM PMSF), then incubated at 4° C. for 60 minutes with gentle shaking, then centrifuged at 4° C. for 5 minutes. The supernatant was collected, aliquoted, and stored at −80° C. Protein was quantitated using Bio-Rad Protein Assay. Binding reactions were performed by incubating 10 µg of each nuclear extract with 1 ng of $^{32}P$ end labeled p53CON and 1 µg of Poly(dI-dC) in binding buffer (20 mM HEPES, pH 7.9, 0.25 M EDTA, 50 µM KCl, 1 mM DTT, 1 mM PMSF, 10% (v/v) glycerol) at room temperature for 20 minutes. 1 µg of the anti-p53 mouse monoclonal antibody DO-1 (Santa Cruz) was then added to each reaction and incubated at room temperature for 30 minutes. Samples were then electrophoresed on a 5% polyacrylamide gel containing Tris borate/EDTA buffer.

Immunoprecipitation SDS-PAGE analysis: A549 cells were cultured in 60 mm dishes at 80% confluence, washed with PBS and starved for 1 hour in phosphate-free DMEM containing 5% fetal bovine serum. Cells were then treated with mismatched control ODN or ISIS 15534 as described, 3 dishes per group, with 0.2 mCi/ml $^{32}Pi$ added into the media. Six hours after treatment, cells were collected and washed with ice-cold PBS and stored at −80° C. prior to analysis. Cell lysates were prepared by incubating the thawed cells at 4° C. for 1 hour in a buffer containing 1% Nonidet P-40, 0.5% sodium deoxycholate, 150 mM sodium chloride, 5 mM EDTA, 1 mM sodium pyrophosphate, 50 mM sodium fluoride, 1 mM PMSF, 5 µg/ml leupeptin, 5 µg/ml aprotinin, and 50 mM Tris-HCl, pH 8.0. Insoluble debris was removed by centrifugation at 3000 rpm at 4° C. for 15 minutes. The supernatants were collected and pre-cleared by incubation with 1.2 µg of normal mouse IgG (Santa Cruz) and 20 µl of protein A-agarose for 1 hour at 4° C. followed by centrifugation at 1500 rpm at 4° C. for 5 minutes. The concentration of cell lysates was then determined using Bio-Rad Protein Assay, and equal amounts of protein from lysates were subjected to immunoprecipitation by incubating with 1 µg of the anti-p53 mouse monoclonal antibody DO-1 (Santa Cruz) for 2 hours at 4° C. Twenty µl of protein A-agarose was added and the mixtures were incubated for 16 hours at 4° C. with rocking. The agarose beads were precipitated by centrifugation and washed five times with 1 ml of ice-cold RIPA buffer. After final wash, the pellet was resuspended in 40 µl electrophoresis sample buffer, boiled for 3 minutes, and analyzed by 10% SDS-PAGE. The bands were visualized by autoradiography.

EXAMPLE I

Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3H$-1,2-benzodithiole-3-one 1,1-dioxide in acetonitrile for the stepwise thiation of the phosphite linkages. The thiation cycle wait step was increased to 68 seconds and was followed by the capping step.

2'-methoxy oligonucleotides were synthesized using 2'-methoxy β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va.

2'-fluoro oligonucleotides were synthesized as described in Kawasaki et al. 1993. Briefly, the protected nucleoside $N^6$-benzoyl-2'-deoxy-2'-fluoroadenosine was synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9-β-D-arabinofuranosyladenine was selectively protected in moderate yield as the 3',5'-ditetrahydropyranyl (THP) intermediate. Deprotection of the THP and $N^6$-benzoyl groups was accomplished using standard methodologies and standard methods were used to obtain the 5'-dimethoxytrityl-(DMT) and 5'-DMT-3'-phosphoramidite intermediates.

The synthesis of 2'-deoxy-2'-fluoroguanosine was accomplished using tetraisopropyldisiloxanyl (TPDS) protected 9-β-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

Synthesis of 2'-deoxy-2'-fluorouridine was accomplished by the modification of a literature procedure in which 2,2'-anhydro-1-β-D-arabinofuranosyluracil was treated with 70% hydrogen fluoride-pyridine. Standard procedures were used to obtain the 5'-DMT and 5'-DMT-3'phosphoramidites.

2'-deoxy-2'-fluorocytidine was synthesized via amination of 2'-deoxy-2'-fluorouridine, followed by selective protection to give $N^4$-benzoyl-2'-deoxy-2'-fluorocytidine. Standard procedures were used to obtain the 5'-DMT and 5'-DMT-3'phosphoramidites.

2'-(2-methoxyethyl)-modified amidites are synthesized according to Martin 1995. For ease of synthesis, the last nucleotide was a deoxynucleotide. 2'-O—$CH_2CH_2OCH_3$-cytosines may be 5-methyl cytosines.

Synthesis of 5-Methyl cytosine monomers:

2,2'-Anhydro[1-(β-D-arabinofuranosyl)-5-methyluridine]:

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine:

2,2'-Anhydro-5-methyluridine (195 g, 0.81 M), tris(2-methoxyethyl)borate (231 g, 0.98 M) and 2-methoxy-ethanol (1.2 L) were added to a 2 L stainless steel pressure vessel and placed in a pre-heated oil bath at 160° C. After heating for 48 hours at 155-160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine:

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine:

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1) Pure product fractions were evaporated to yield 96 g (84%).

3'-O-Acetyl-2'-O-methoxyethyl-5'-O-dimethoxytrityl-5-methyl-4-triazoleuridine:

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. POCl$_3$ was added dropwise, over a 30 minute period, to the stirred solution maintained at 0-10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 ML of saturated NaCl, dried over sodium sulfate and evaporated. The residue was triturated with EtOAc to give the title compound.

2'-O-Methoxyethyl-5'-O-dimethoxytrityl-5-methylcytidine:

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH3 gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-0-methoxyethyl-5'-O-dimethoxytrityl-5-methylcytidine:

2'-O-Methoxyethyl-5'-0-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite:

N$^4$-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (tic showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi et al. 1993a) using commercially available phosphoramidites (Glen Research, Sterling Va. or Chem-Genes, Needham Mass.).

Oligonucleotides having methylene(methylimino) backbones are synthesized according to U.S. Pat. No. 5,378,825. Other nitrogen-containing backbones are synthesized according to WO 92/20823.

Oligonucleotides having amide backbones are synthesized according to De Mesmaeker et al. 1995. The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to Nielsen et al. 1991.

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al. 1991. Results obtained with HPLC-purified material were similar to those obtained with non-HPLC purified material.

EXAMPLE II

Antisense Oligonucleotides for PP5 Expression

Because there are no truly specific inhibitors of any known mammalian PPases, methods were first developed to distinguish events mediated by PP5 from those mediated by the other closely related PPases. For this purpose, antisense oligonucleotides (ODNs) targeting human PP5 were developed to specifically inhibit PP5 gene expression. To accomplish this, 13 ODNs were initially synthesized, each 20 bases in length, targeting specific regions in the 5'-untranslated region, the protein coding region or the 3'-untranslated region of human PP5 mRNA (see FIG. 1 and Table 1). These oligonucleotides are "chimeric" oligonucleotides containing 8 central phosphorothioate oligodeoxy residues ("oligodeoxy gap") flanked by 6 2'-methoxyethyl residues on the 3' and 5' ends of the oligonucleotide (Dean and Griffey 1997) (see Table 1 where the flanking residues are shown in bold). All cytosines in the 2'-MOE wings are 5-methylcytosines. The oligonucleotides shown in Table 1 were designed using the Genbank sequences HSSERTHRP (Genbank accession number X92121), HSRNAPPP5 (Genbank accession number X89416) and PPP5C (Genbank accession number U25174), synthesized and tested for inhibition of PP5 mRNA expression in A549 cells using a Northern blot assay.

Additional oligonucleotides targeted to PP5 and having SEQ ID NO: 1 were synthesized. These are chimeric oligonucleotides having slightly wider deoxy gaps (and shorter 2'-MOE wings, shown in bold in Table 2) than ISIS 14504. These oligonucleotides are shown in Table 2, along with ISIS 15521, a mismatch control. These oligonucleotides differ in their backbone composition; ISIS 15523 is uniformly phosphorothioate (P=S) and ISIS 15534 is a mixed backbone compound with a phosphodiester backbone (P=O) in the wings and phosphorothioate (P=S) in the deoxy gap. ISIS 15521, the mismatch control, is also a mixed backbone compound with phosphodiester wings and a phosphorothiate gap.

An additional oligonucleotide targeted to PP5 and having SEQ ID NO: 1 was synthesized. This compound, ISIS 15516, has a phosphorothioate backbone and is a chimeric oligonucleotide having a slightly wider deoxy gap (and shorter 2'-MOE wings, shown in bold in Table 3) than ISIS 14493. These oligonucleotides are shown in Table 3, along with ISIS 15517, a mismatch control with a mixed backbone (P=S in the gap, P=O in the wings).

EXAMPLE III

Effect of Antisense Oligonucleotides on PP5 Expression

The oligonucleotides showin in Table 1 were tested for inhibition of PP5 mRNA expression. In the initial screen, A549 cells were treated with oligonucleotides at a concentration of 300 nM oligonucleotide for four hours in the presence of 20 mg/ml lipofectin. Results were normalized and expressed as a percent of control. The effect of each oligonucleotide on levels of PP5 mRNA, expressed as approximate percent inhibition compared to control, is shown in Table 1. In this initial screen, oligonucleotides giving a reduction of PP5 mRNA of approximately 50% or greater were considered active. According to this criterion, oligonucleotides 14493, 14494, 14495, 14496, 14498, 14499 and 14504 were found to be active. These sequences (SEQ ID NO: 3, 4, 5, 6, 8, 9 and 1, respectively, SEQ ID Nos shown in bold in Table 1) are therefore preferred. Of these, oligonucleotides 14493, 14498 and 14504 (SEQ ID NO: 3, 8 and 1, respectively) showed at least 70% inhibition of PP5 mRNA in this assay and are highly active.

The oligonucleotides shown in Table 2 were also tested for their ability to reduce PP5 mRNA levels in A549 cells, using oligonucleotide doses of 25 to 500 nM. ISIS 15523 demonstrated an $IC_{50}$ of approximately 100 nM, and ISIS 15534 demonstrated an $IC_{50}$ of approximately 135 nM. The mismatch control, ISIS 15521, did not inhibit PP5 mRNA levels by more than 20% at any of the doses tested.

ISIS 15516 and 15517 oligonucleotides (see Table 3) were also tested for their ability to reduce PP5 mRNA levels in RINm5f cells. Dose response curves were generated for oligonucleotide doses of 25 to 500 nM. ISIS 15516 demonstrated an $IC_{50}$ of approximately 135 nM. The scrambled control, ISIS 15517, gave less than 10% reduction of PP5 mRNA levels at any dose tested.

Figure 2:
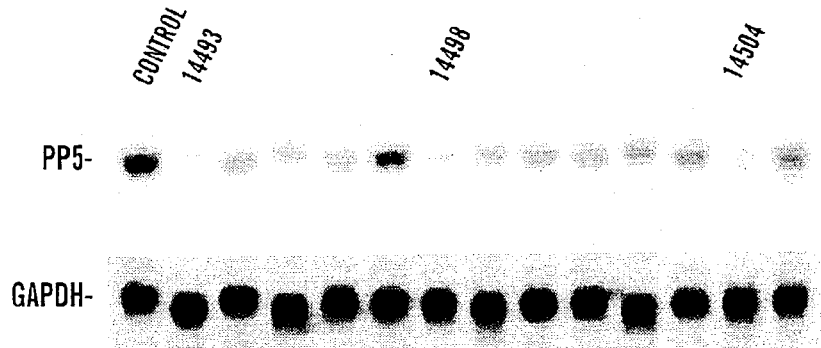
FIG. 2 is a Northern-blot analysis probing for levels of PP5 and G3DPH mRNA after treatment with the indicated antisense ODNs.
Figure 3:
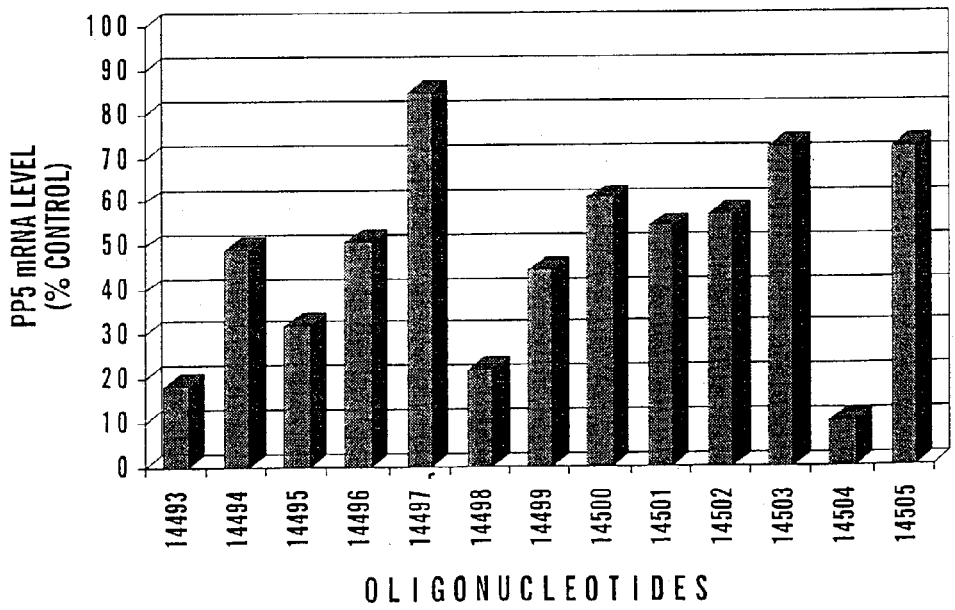
FIG. 3 shows PP5 mRNA levels from the Northern blot analysis (FIG. 2) expressed as a percentage of the levels of PP5 mRNA in control cells following normalization to G3DPH.

As discussed above, each oligo was tested for its ability to specifically inhibit the expression of PP5. Since these ODNs generally act through a RNase H-dependent mRNA cleavage mechanism in cells (Crooke 1993), the activity of each oligo was initially determined by Northern blot analysis probing for levels of PPase mRNA (FIG. 2). Specifically, A549 cells were treated with the indicated antisense ODNs at a concentration of 300 nM as previously described (Dean et al. 1994). RNA was prepared 24 hours later and analyzed for PP5 and G3DPH mRNA levels by Northern blot analysis. Control cells were treated with a random ODN. FIG. 3 shows PP5 mRNA levels from the Northern blot analysis (FIG. 2) expressed as a percentage of the levels of PP5 mRNA in control cells following normalization to G3DPH.

Comparison of the levels of PP5 expression in A549 lung carcinoma cells treated with the antisense PP5 specific ODNs identified several target sequences, and ISIS 14504 was chosen for further development. To increase the potency of ISIS 14504, the "oligodeoxy gap" region was increased from eight to ten contiguous phosphorothioate nucleotides, and the new ODN, ISIS 15534, proved more potent than ISIS 14504, causing a dose-dependent reduction of PP5 mRNA levels with an $IC_{50} \approx 50$ nM (FIGS. 4 and 5). No effects on PP5 mRNA levels were observed with mismatched control analogues (i.e. ISIS 15521). Specifically, A549 cells were treated with increasing concentrations (25-500 nM) of ISIS 15534 (SEQ ID NO: 1: GGGCCCTAT-TGCTTGAGTGG) or a mismatched control analogue, ISIS 15521 (SEQ ID NO: 2: GTGCGATCGTTGCGGTTAGC) that contains 13 base changes (mismatches) within the 15534 sequence. Total mRNA was prepared 24 hours later and analyzed for PP5 and G3PDH mRNA levels by Northern blot analysis: (−) indicates untreated cells (FIG. 4). FIG. 5 shows the quantification of PP5 mRNA levels after normalization to G3PDH in A549 cells following treatment with increasing concentrations of ISIS 15534 (solid square) or a mismatched control analogue of ISIS 15534, ISIS 15521 (solid circle). Referring to FIG. 6, Western blot analysis of PP5 protein levels in A549 cells indicated that the treatment of cells with ISIS 15534 effectively decreases PP5 protein levels in <18 hours. Cells were treated with ISIS 15534 (1) or the mismatch control ODN (2) at a concentration of 300 nM, and protein extracts were prepared 24 hours later. Each lane contained 40 μg of protein. In addition, ISIS 15534 is highly specific, having no effect on the levels of PP1, PP2A or PP4 mRNA (FIG. 7). A549 cells were treated with increasing concentrations (25-500 nM) of ISIS 15534, and total mRNA was prepared 24 hours later and analyzed for PP1, PP2A, and PP4 mRNA levels by Northern blot analysis. Similar effects were also observed with T-24 bladder carcinoma cells and TR9-7 human fibroblasts.

EXAMPLE IV

Effect of Antisense Inhibition of PP5 Expression on Cell Cycle Progression.

Figure 8:
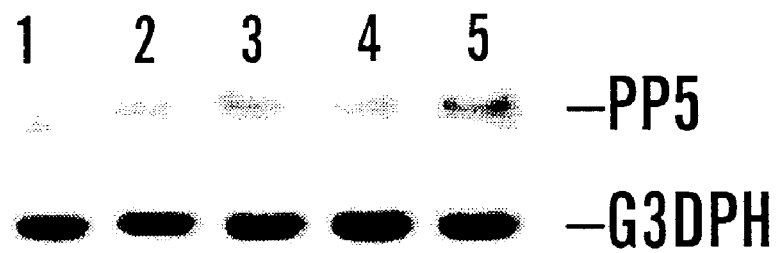
FIG. 8 shows the recovery of PP5 mRNA with time after treatment with ISIS 15534.
Figure 9:
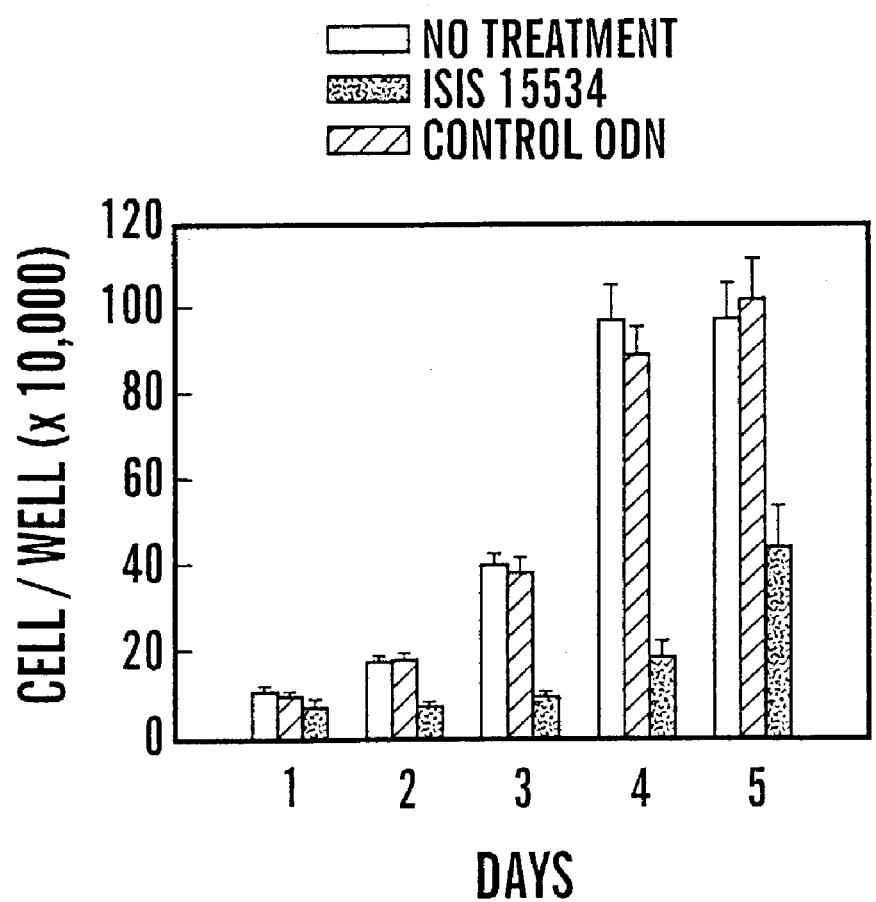
FIG. 9 shows a time course for the antiproliferative effects of ISIS 15534 and the mismatch control ODN, ISIS 15521.

Having obtained suitable methods for specifically inhibiting PP5 gene expression, the role of PP5 in cell cycle progression was next examined. As a first step, A549 cells were treated with a single-treatment of ISIS 15534 at a concentration of 300 nM. FIG. 8 shows the recovery of PP5 mRNA with time after treatment of the A549 cells with ISIS 15534 at time 0. At days 1, 2, 3, 4, and 5 total mRNA was prepared and analyzed for PP5 and G3DPH mRNA levels by Northern blot analysis. As shown in FIG. 9, this treatment had a marked effect on cell proliferation over a 5 day period. Growth is completely inhibited for three days, and the recovery of proliferation rate at days 4 and 5 correlates well with the recovery of PP5 mRNA expression due to the extrusion of ODNs from the cell and nuclease-mediated degradation of ISIS 15534 following a single application of the ODNs. A similar effect was not observed with the mismatched control ODN. Specifically, cells in log phase growth were treated with a single dose (300 nM) at time zero with ISIS 15534 or the mismatched control ODN analogue of ISIS 15534 (ISIS 15521). Cell number was determined after days 1, 2, 3, 4, and 5 following treatment. Each point represents the mean of triplicate cultures with error bars representing the SD. On days 2, 3, 4 and 5, ISIS 15534-treated cells showed a decrease in proliferation of 55%, 75%, 89% and 55%, respectively, compared to control.

Flow cytometry analysis of cells treated with ISIS 15534 indicates that growth arrest occurs prior to the onset of DNA synthesis, suggesting that PP5 expression is necessary prior to the initiation of the S-phase of the cell cycle. Thus, several possible mechanisms by which PP5 could affect known pathways leading to G1 growth arrest (Sherr 1994) were examined. These studies revealed that the inhibition of PP5 expression has a marked effect on the expression of the Cdk inhibitor p21$^{WAF1/Cip\ 1}$, which is apparent from the dose-dependent correlation between the inhibition of PP5 expression and an increase in p21$^{WAF1/Cip\ 1}$ mRNA shown in FIGS. 10-12. In FIGS. 10 and 11, A549 cells in log phase growth were treated with increasing concentrations (25-500 nM) of ISIS 15534 (FIG. 11) or a mismatched control (ISIS 15521) analogue of ISIS 15534 (FIG. 10). Total mRNA was prepared 24 hours later and analyzed for PP5, p21$^{WAF1/Cip\ 1}$ and G3PDH mRNA levels by northern blot analysis. FIG. 12 shows the quantification of PP5 mRNA and p21$^{WAF1/Cip\ 1}$ mRNA levels after normalization to G3PDH mRNA levels in A549 cells following treatment with increasing concentrations of ISIS 15534 (solid square and open square) or a mismatched control analogue of ISIS 15534 (solid circle and open circle). Solid symbols indicate PP5 mRNA and open symbols indicate p21$^{WAF1/Cip\ 1}$ mRNA.

To further characterize the relationship of PP5 and p21$^{WAF1/Cip\ 1}$, changes in p53 expression following treatment with UV-radiation or ODNs that inhibit the expression of PP5 were compared. Northern analysis of p53, PP5 and p21$^{WAF1/Cip\ 1}$ mRNA levels in A549 cells following treatment with ISIS 15534 revealed that the induction of p21$^{WAF1/Cip\ 1}$ expression occurs without an apparent change in the amount of p53 mRNA (FIG. 13). In contrast, as reported previously (Wu and Levine 1997), following UV-radiation treatment the expression of both p53 and p21$^{WAF1/Cip\ 1}$ is induced, and interestingly, the level of PP5 mRNA is reduced (FIG. 13). This suggests that ISIS 15534 may induce the expression of p21$^{WAF1/Cip\ 1}$ via a mechanism that does not require the induction of the p53 gene. Specifically, referring to FIG. 13, A549 cells were treated with nothing (UV; C), 50 Jm$^{-2}$ of UV-radiation (UV, T), a mismatched control ODN (ISIS-15534; C), or ISIS 15534 (ISIS-15534; T), and 6 hours (UV) or 24 hours (ISIS 15534) later the total RNA was prepared and analyzed for p53, PP5, p21$^{WAF1/Cip\ 1}$ and G3PDH mRNA levels by northern blot analysis. To determine if the inhibition of PP5 gene expression can induce the expression of p21$^{WAF1/Cip\ 1}$ via a p53 independent pathway, the effects of ISIS 15534 in p53 deficient T-24 human bladder cancer cells (Kawasaki et al. 1994; Cooper et al. 1994) was tested. As seen in FIG. 14, although the amount of PP5 mRNA is clearly reduced, the induction of p21$^{WAF1/Cip\ 1}$ is not observed in T-24 cells following treatment with ISIS 15534. Furthermore, unlike the observations in A549 cells, treatment of T-24 cells with ISIS 15534 does not effectively induce G1-growth arrest. This suggests that the ability of ISIS 15534 to induce p21$^{WAF1/Cip\ 1}$ expression arises via a pathway that is dependent on the presence of p53 yet does not require an increase in p53 expression, and PP5 acts upstream of p53 in this pathway. Specifically, T-24 cells were treated with mismatch control ODN (C) or ISIS 15534 (T) and 24 hours later the total RNA was analyzed by northern blot analysis as described above.

To explore the possibility that PP5 expression is related to the activation of p53 without an increase in p53 gene transcription, the ability of ISIS 15534 to affect p21$^{WAF1/Cip\ 1}$ transcription in TR9-7 cells was then tested. TR9-7 cells are a stable cell line derived from MDAH041 p53-null human fibroblasts that contain tetracycline-regulated transactivator and operator plasmids to control the expression of wild-type p53 (Agarwal et al. 1995; Yin et al. 1992). When TR9-7 cells are grown in the presence of 1 μg tetracycline, p53 protein is expressed at a very low level, which is insufficient to induce p21$^{WAF1/Cip\ 1}$ or cell cycle arrest (Agarwal et al. 1995; Yin et al. 1992). Treatment of TR9-7 cells grown in the presence of tetracycline with ISIS 15534 inhibits the expression of PP5 mRNA, induces the expression of p21$^{WAF1/Cip\ 1}$ mRNA, and induces growth arrest without a corresponding increase in the expression of p53 mRNA (FIG. 15). In contrast, in p53-null human fibroblasts (TR9; FIG. 15), as also observed in p53 deficient T-24 human bladder cancer cells (FIG. 14), treatment with ISIS 15534 inhibits the expression of PP5 mRNA without inducing p21$^{WAF1/Cip\ 1}$ or G1-growth arrest (FIG. 15). Specifically, TR9-7 cells were grown in the presence of 0.8 μg/ml of tetracycline to keep the expression of p53 below the threshold necessary for the induction of p21$^{WAF1/Cip\ 1}$ (Agarwal et al. 1995; Yin et al. 1992) and treated with mismatch control ODN (C) or ISIS 15534 (T) at a concentration of 300 nM. Total RNA was prepared 24 hours later and analyzed by northern blot analysis as described above. These studies add additional support to the theory that ISIS 15534 induces G1-growth arrest by inhibiting the expression of PP5, which then induces p21$^{WAF1/Cip\ 1}$ expression via a pathway that requires p53 but does not require an increase in p53 gene transcription.

Further evidence for the involvement of p53 in ISIS 15534 mediated p21$^{WAF1/Cip\ 1}$ induction and growth arrest comes from mobility gel shift analysis and immunoprecipitation studies in A549 cells. Following treatment with ISIS 15534, gel-shift analysis indicates that the ability of p53 to bind DNA is enhanced when the expression of PP5 is inhibited (FIG. 16). Specifically, nuclear extracts were prepared from A549 cell cultures treated with mismatched control ODN (ISIS 15521) or ISIS 15534 as described above. After 6 hours the ability of p53 to bind DNA was analyzed by gel-mobility shift assay (see Materials and Methods) Lane 1, no protein control: migration of $^{32}$P-p53CON probe in the absence of nuclear extracts; Lane 2, mismatched control ODN: nuclear extracts prepared from mismatch control ODN treated cells; Lane 3, ISIS 15534: nuclear extracts from cells treated with ISIS 15534; Lane 4, excess cold probe control: samples treated in an identical manner as in lane 3 incubated in the presence of excess cold p53CON probe.

In addition, immunoprecipitation of p53 from [$^{32}$P] equilibrated cells reveals that treatment with ISIS 15534 markedly enhances the phosphorylation state of p53 (FIG. 17), and recombinant PP5 can dephosphorylate p53 in vitro. Specifically, A549 cells were cultured in [$^{32}$Pi] and treated with ISIS 15534 or mismatch control ODN. Six hours later, the protein extracts were prepared, and changes in p53 phosphorylation were determined by immunoprecipitation SDS-PAGE analysis and visualized by autoradiography (see Materials and Methods). Lane 1, p53 from cells treated with mismatched control ODN; Lane 2, p53 from cells treated with 300 nM ISIS 15534.

These studies suggest that one of the biological functions of PP5 is to regulate the phosphorylation state of p53, which in turn influences the ability of p53 to bind DNA.

From previous studies and the studies described here, one concludes that the inhibition of PP5 gene expression is capable of inducing growth arrest in the G1-phase of the cell cycle by enhancing p53-mediated expression of p21$^{WAF1/Cip\ 1}$ in the absence of p53 gene transcription. This indicates that PP5 is an upstream regulator of p53 in a pathway(s) leading to p21$^{WAF1/Cip\ 1}$ mediated G1-growth arrest. The inhibition of PP5 expression alone is sufficient to trigger the expression of p21$^{WAF1/Cip\ 1}$ and growth arrest, providing the first direct evidence for the involvement of a specific mammalian PPase in G1-growth arrest. The decrease in PP5 mRNA levels following UV-treatment may also suggest a role for PP5 in a p53 mediated response to DNA damage (UV-radiation→↓PP5→p53active→↑p21WAF1/Cip 1→G1-growth arrest).

Recent studies indicate that the functional expression of the human p21WAF1/Cip 1 gene in rat glioma cells suppresses tumor growth in vivo (Hsiao et al. 1997), and the survival of patients with advanced gastric carcinoma correlates with the expression of p21WAF1/Cip 1 (Gomyo et al. 1997). When considered together with the data presented herein, these studies indicate that inhibitors of PP5 gene expression may be useful to elevate the level of p21WAF1/Cip 1 expression in cells harboring functional defects in p53 or BRCA1 mediated pathways to restore G1 checkpoint growth control. Thus, compounds that inhibit the expression and/or activity of PP5 may be used clinically as an alternative therapy for the treatment of human cancers in which the ability to induce p21WAF1/Cip 1 has been diminished or lost. Since defects in p53 mediated pathways are associated with >50% of all human cancers, the development of compounds that induce the expression of genes down stream of p53 to restore G1-growth control may, therefore, have a major impact on the treatment of many human cancers.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

| ISIS # | SEQUENCE (5' to 3') | PERCENT INHIBITION | SEQ ID NO: |
|---|---|---|---|
| 14493 | TCGCCCTCCGCCATCGCCAT | 84% | 3 |
| 14494 | TTCAGAGCTCCATCAGCCGG | 52% | 4 |
| 14495 | GTAGGCCAGGCTGCGGTTGC | 66% | 5 |
| 14496 | CCGCTGTACTCATCCTCAAT | 54% | 6 |
| 14497 | TCCCCACATACTGTAATCTT | 11% | 7 |
| 14498 | GTACTTGGCCTTCACCTCAC | 80% | 8 |
| 14499 | CCAGGTTGTTCTCTTCCAAG | 62% | 9 |
| 14500 | AGAGCCCTGGAGGTGGATGT | 41% | 10 |
| 14501 | CGCCCCGCCCGTCACCTCAC | 42% | 11 |
| 14502 | CCTACCCCTCTGCAAACCT | 40% | 12 |
| 14503 | GCCCCAGCTGCTCCACCTCC | 27% | 13 |
| 14504 | GGGCCCTATTGCTTGAGTGG | 92% | 1 |
| 14505 | CCCAGCCTAGCCCCACCATG | 23% | 14 |

TABLE 2

| ISIS # | SEQUENCE (5' to 3') | BACKBONE | SEQ ID NO: |
|---|---|---|---|
| 15523 | GGGCCCTATTGCTTGAGTGG | P=S | 1 |
| 15534 | GGGCCCTATTGCTTGAGTGG | P=O/P=S | 1 |
| 15521 | GTGCGATCGTTGCGGTTAGC | P=O/P=S | 2 |

TABLE 3

| ISIS # | SEQUENCE (5' TO 3') | BACKBONE | SEQ ID NO: |
|---|---|---|---|
| 14493 | TCGCCCTCCGCCATCGCCAT | P=O/P=S | 3 |
| 15516 | TCGCCCTCCGCCATCGCCAT | P=S | 3 |
| 15517 | GCTCTACTCCGCCCCATGCC | P=O/P=S | 15 |

REFERENCES

Agarwal, M. L., et al., Proc Natl Acad Sci USA 92:8493 (1995).
Bastians, H., and Ponstingl, H., J Cell Sci 109:2865 (1996).
Berge, et al., J of Pharma Sci 66:1 (1977).
Bialojan, A., and Takai, A., Biochem J 256:283 (1988).
Brewis, N. D., EMBO J 12:987 (1993).
Chen, M. X., et al., EMBO J 12:4278-4290 (1994).
Chernova, B. O., et al., Trends Bio Sci 20:431 (1995).
Chiang, et al., J Biol Chem. 266:18162-18171 (1991).
Cohen, P., Annu Rev Biochem 58:453 (1989).
Cohen, P., Trends Biochem Sci 22:245 (1997).
Cohen, P., et al., FEBS Lett 268:355 (1990a).
Cohen, P., et al., Trends Bio Sci 15:98 (1990b).
Cooper, M. J., et al., Oncol Res 6:569 (1994).
Crooke, S. T., Annu Rev Pharmacol Toxicol 32:329 (1993).
Dean, N. M., and Griffey, R. G., Antisense Nucleic Acid Drug Dev 7:229 (1997).
Dean, N. M., et al., J Biol Chem 269:16416 (1994).
De Mesmaeker, et al., Acc Chem Res 28:366-374 (1995).
Duttaroy, A., et al., J Cell Biochem 64:434 (1997).
Dynlacht, B. D., Nature 389:149 (1997).
Egloff, M. P., et al., J Mol Biol 254:942 (1995).
Elledge, S. J., and Harper, J. W., Curr Opin Cell Biol 6:874 (1994).
Gebeyehu, G., et al., Nucl Acids Res 15:4513 (1987).
Gomyo, Y., et al., Cancer 79:2067 (1997).
Gottlieb, T. M., and Oren, M., Biochim Biophys Acta 1287:77 (1996).
Gu, Y., et al., Nature 366:707 (1993).
Harper, J. W., et al., Mol Biol Cell 6:387 (1995).
Hecker, D., et al., Oncogene 12:953 (1996).
Honkanen, R. E., et al., J Biol Chem 265:19401 (1990).
Honkanen, R. E., et al., Toxicon 32:339 (1994).
Hsiao, M., et al., Biochem Biophys Res Commun 233:329 (1997).
Hunter, T., and Pines, J., Cell 79:573 (1994).
Kabanov, et al., FEBS Lett 259:327 (1990).
Kawasaki, et al., J Med Chem 36:831-841 (1993).
Kawasaki, T., et al., Cancer Lett 82:113 (1994).
Kornberg, A., *DNA Replication*, W. H. Freeman & Co., San Francisco, pp 75-77 (1980).
Lamb, J. R., et al., Trends Bio Sci 20:257 (1995).
Letsinger, et al., Proc Natl Acad Sci USA 86:6553 (1989).
Macleod, K. F., et al., Genes Dev 9:935 (1995).
Manoharan, et al., Ann NY Acad Sci 660:306 (1992).
Manoharan, et al., Bioorg Med Chem Let 3:2765 (1993).
Manoharan, et al., Bioorg Med Chem Let 4:1053 (1994).
Manoharan, et al., Nucleosides & Nucleotides 14:969 (1995a).
Manoharan, et al., Tetrahedron Lett 36:3651 (1995b).
Martin, et al., Helv Chim Acta 78:486-504 (1995).
Mayr, G. A., et al., Cancer Res 55:2401 (1995).
Nielsen, P. E., et al., Science 254:1497 (1991).

Oberhauser, et al., Nucl Acids Res 20:533 (1992).
Peter, M., and Herskowitz; I., Cell 79:181 (1994).
Saison-Behmoaras, et al., EMBO J 10:111 (1991).
Sanghvi, et al., Nucl Acids Res 21:3197-3203 (1993a).
Sanghvi, Y. S., in Crooke, S. T., and Lebleu, B., eds., *Antisense Research and Applications*, CRC Press, Boca Raton, pp 276-278 (1993b).
Scully, R., et al., Cell 90:425 (1997).
Shenolikar, S., and Nairn, A. C., Adv Sec Mess and Phosphopro Res 23:1 (1991).
Sherr, C. J., Cell 79:551 (1994).
Somasundaram, K., et al., Nature 389:187 (1997).
Svinarchuk, et al., Biochimie 75:49 (1993).
Takenaka, I., et al., J Biol Chem 270:5405 (1995).
Walter, G., and Mumby, M., Biochimi Biophys Acta 1155:207 (1993).
Wu, L., and Levine, A. J., Mol Med 3:441 (1997).
Xiong, Y., et al., Nature 366:701 (1993).
Yin, Y., et al., Cell 70:937 (1992).
Zeng, Y. X., and el-Deiry, W. S., Oncogene 12:1557 (1996).

What is claimed is:

1. A method of activating p53 to increase expression of $p21^{WAF1/Cip1}$ in cells, the method comprising:
   selecting cells for decreasing levels of PP5 protein;
   exposing the cells to a compound which decreases levels of PP5 protein in cells in vitro, wherein the compound is an antisense oligonucleotide having a nucleotide sequence of SEQ ID NO:1, SEQ ID NO:3, SEQ ID NO:4, SEQ ID NO:5, SEQ ID NO:6, SEQ ID NO:8, and SEQ ID NO:9 or an inhibitor of the PP5 protein and;
   measuring the levels of PP5 protein in the cells, measuring inhibition of the PP5 protein or measuring proliferation of the cells.

2. The method of claim 1 wherein the inhibitor of the PP5 protein is okadaic acid or microcystin.

3. The method of claim 1 wherein the cells are cancer cells.

4. The method of claim 3 wherein the cancer cells harbor a defect in a tumor suppressor gene that results in decreased induction of $p21^{WAF1/Cip1}$, wherein the tumor suppressor gene is a p53 gene or a BRCA1 gene.

5. A method of treating a subject having a defect in a tumor suppressor gene the method comprising:
   selecting a subject having cells having a defect in a p53 gene or a BRCA1 gene and in which expression of $p21^{WAF1/Cip1}$ is to be increased and
   administering to the subject a compound under conditions effective to activate p53 to increase expression of $p21^{WAF1/Cip1}$ in the cells and decrease levels of PP5 protein in the cells, wherein the compound is an antisense oligonucleotide having a nucleotide sequence of SEQ ID NO:1, SEQ ID NO:3, SEQ ID NO:4, SEQ ID NO:5, SEQ ID NO:6, SEQ ID NO:8, and SEQ ID NO:9.

* * * * *

```
                             SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid (iv) ANTI-SENSE: YES (xi) SEQUENCE DESCRIPTION: SEQ ID NO: 1:

GGGCCCTATT GCTTGAGTGG                                                    20

(2) INFORMATION FOR SEQ ID NO: 2:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid (iv) ANTI-SENSE: YES (xi) SEQUENCE DESCRIPTION: SEQ ID NO: 2:

GTGCGATCGT TGCGGTTAGC                                                    20

(2) INFORMATION FOR SEQ ID NO: 3:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid (iv) ANTI-SENSE: YES (xi) SEQUENCE DESCRIPTION: SEQ ID NO: 3:

TCGCCCTCCG CCATCGCCAT                                                    20

(2) INFORMATION FOR SEQ ID NO: 4:

(i) SEQUENCE CHARACTERISTICS:
           (A) LENGTH: 20 base pairs
           (B) TYPE: nucleic acid
           (C) STRANDEDNESS: single
```

```
        (D) TOPOLOGY: linear (ii) MOLECULE TYPE: other nucleic acid (iv) ANTI-SENSE: YES (xi) SEQUENCE DESCRIPTION: SEQ ID NO: 4:

TTCAGAGCTC CATCAGCCGG                                              20

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 5:

GTAGGCCAGG CTGCGGTTGC                                              20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 6:

CCGCTGTACT CATCCTCAAT                                              20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 7:

TCCCCACATA CTGTAATCTT                                              20

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 8:

GTACTTGGCC TTCACCTCAC                                              20
```

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 9:

CCAGGTTGTT CTCTTCCAAG                                                20

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 10:

AGAGCCCTGG AGGTGGATGT                                                20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 11:

CGCCCCGCCC GTCACCTCAC                                                20

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 12:

CCTACCCCCT CTGCAAACCT                                                20

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES -continued (xi) SEQUENCE DESCRIPTION: SEQ ID NO: 13:

GCCCCAGCTG CTCCACCTCC                                                                               20

(2) INFORMATION FOR SEQ ID NO: 14:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid (iv) ANTI-SENSE: YES (xi) SEQUENCE DESCRIPTION: SEQ ID NO: 14:

CCCAGCCTAG CCCCACCATG                                                                               20

(2) INFORMATION FOR SEQ ID NO: 15:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid (iv) ANTI-SENSE: YES (xi) SEQUENCE DESCRIPTION: SEQ ID NO: 15:

GCTCTACTCC GCCCCATGCC                                                                               20